United States Patent [19]

Bambara

[11] Patent Number: 5,029,477
[45] Date of Patent: Jul. 9, 1991

[54] INTEGRITY TEST FOR ACOUSTIC BEARING DEFECT DETECTOR

[75] Inventor: Joseph E. Bambara, North Babylon, N.Y.

[73] Assignee: Servo Corporation of America, Hicksville, N.Y.

[21] Appl. No.: 472,737

[22] Filed: Jan. 31, 1990

[51] Int. Cl.$^5$ .............................................. G01N 29/04
[52] U.S. Cl. ........................................ 73/660; 381/56; 381/58; 246/169.5
[58] Field of Search .................... 73/660; 246/169 S; 379/37, 39; 324/207.16, 221; 381/58, 56

[56] References Cited

U.S. PATENT DOCUMENTS

| | | | |
|---|---|---|---|
| 3,956,693 | 5/1976 | Zutrauen et al. | 324/207.16 |
| 4,454,502 | 6/1984 | Fahey et al. | 379/37 |
| 4,649,344 | 3/1987 | Moll et al. | 324/221 |
| 4,790,190 | 12/1988 | Bambara et al. | 73/660 |
| 4,843,885 | 7/1989 | Bambara | 73/660 |

FOREIGN PATENT DOCUMENTS 0173928  7/1988  Japan ..................................... 73/660

Primary Examiner—Jin F. Ng
Assistant Examiner—Sylvia Chen
Attorney, Agent, or Firm—Kane, Dalsimer, Sullivan, Kurucz, Levy, Eisele & Richard

[57] ABSTRACT

This invention relates to the testing of apparatus used for on-line acoustic detection of bearing defects, particularly in railroad applications. A loudspeaker on each side of the section of track, in response to a microprocessor, generates simulated acoustic signatures characteristics of various bearing defects. The microprocessor additionally sends corresponding simulated train speed signals to the apparatus. The invention monitors the apparatus for the appropriate alarm signal.

17 Claims, 3 Drawing Sheets

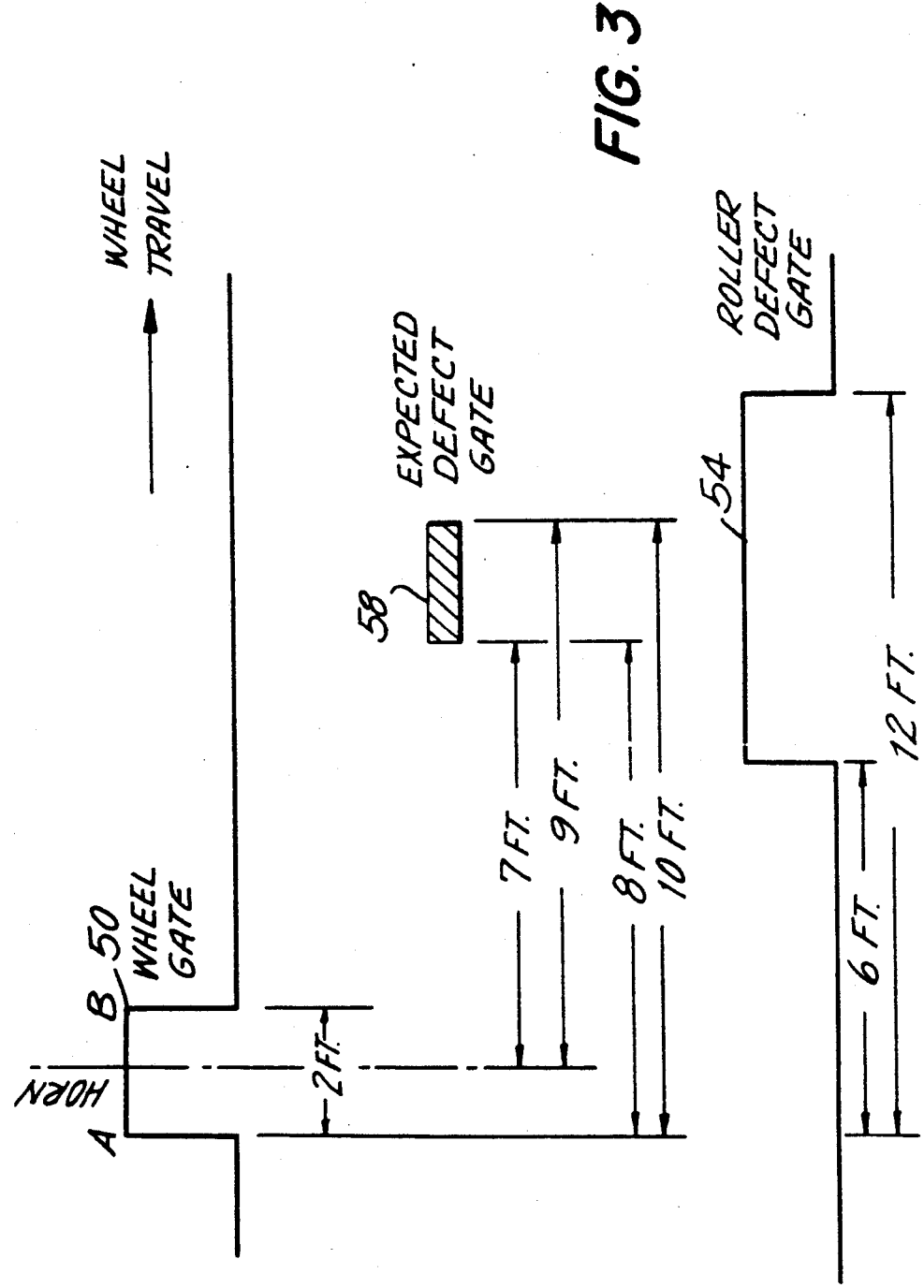

INTEGRITY TEST FOR ACOUSTIC BEARING DEFECT DETECTOR

BACKGROUND OF THE INVENTION

1. Field of Invention

The present invention relates to bearing defect detectors and in particular to an integrity test for an acoustic system for detecting defects in the bearings of moving railroad cars.

2. Description of the Prior Art

Heretofore, the detection of defects in railway car bearings has relied upon stationary infrared sensing means along railroad tracks to detect an abnormal heat rise associated with bearing failure in passing railroad cars. While such systems have enjoyed widespread use and an industry-wide reputation for reliability, they suffer from a serious drawback in that they detect a defect only after a damaging heat build-up has occurred within the bearing. Furthermore, this heat build-up often does not occur until a total bearing failure is imminent, thereby normally warranting an immediate stopping of the train so that an emergency field repair may be done. As this requires a delay in the train until a repair team may arrive with the necessary equipment, the total cost of this procedure can be very high.

From U.S. Pat. Nos. 4,790,190 and 4,843,885 along with pending patent application Ser. No. 367,890 filed July 6, 1989 it is known that defects in tapered roller bearings, such as those used in railroad cars, produce sounds during operation at characteristic frequencies dependent upon the location or type of defect (i.e., at the bearing cup, cone, or roller), the combination of the size of the wheel and the bearing capacity (frequently encountered combinations on railroads are a 28 inch wheel with a 70 ton capacity bearing, a 33 inch wheel with a 70 ton capacity bearing, and a 36 inch wheel with a 100 ton capacity bearing), and the speed of the train.

Additionally, irregularities in the wheel circumference ("flats") produce a characteristic frequency dependent upon wheel rotational frequency.

Thus for any given train speed, a defective bearing will produce a sound at a characteristic frequency dependent upon the location of the defect in the bearing and the combination of the train speed, wheel size and bearing capacity. Wheel flats will produce a sound at additional characteristic frequencies depending on train speed and wheel size.

Furthermore, it is known from the aforementioned references that the sounds emanating from a defective bearing are amplitude modulated on a carrier frequency in the 10–12 kilohertz range. Therefore, these references disclose a method and apparatus for on-line testing of bearing defects using amplitude demodulation to remove extraneous sounds from electronic analysis as the train passes the apparatus. This allows testing to be done at diverse, possibly isolated, locations throughout the railroad system notwithstanding inclement weather or other obstacles. While this apparatus and method has shown great utility, there is a need to be able to self-test the electronic apparatus automatically and efficiently. In some cases, the test may be monitored from a centralized location, unimpeded by weather conditions or the isolation of the apparatus. Furthermore, the test may be initiated at regular intervals or immediately before and/or after the passage of a train.

OBJECTS AND SUMMARY OF INVENTION

It is therefore an object of this invention to provide for the automated testing of apparatus for the on-line acoustic detection of bearing defects, particularly for apparatus using amplitude demodulation for detection of frequencies characteristic of various railway bearing defects.

It is therefore a further object of this invention to provide for automated self-testing which may be monitored from a central location, of remotely placed apparatus for the on-line acoustic detection of bearing defects.

This invention includes two loudspeakers. Each loudspeaker is directly across from the acoustic sensor dedicated to one of the two rails (i.e., the loudspeaker adjacent to rail 1 is monitored by the acoustic sensor adjacent to rail 2 and the loudspeaker adjacent to rail 2 is monitored by the acoustic sensor adjacent to rail 1). A microprocessor control unit drives each loudspeaker and associated driver amplifier, one at a time, to produce sounds simulating the characteristic acoustic signature of the various bearing defects. The microprocessor sets the circuitry of the aforementioned references (non-limiting examples of this circuitry typically include a bandpass filter, demodulator, and spectrum analyzer or the functional equivalents thereof) to the train speed corresponding to the simulated characteristic acoustic signature. The simulated acoustic signatures may be generated in a simple mode without any timing or predetermined timing delay zones into which the resulting alarms are expected to fall. Alternately, the simulated acoustic signatures may be timed so as to be generated within a preselected "wheel gate", and the resulting alarm is expected to occur within a predetermined delay zone (i.e., a "bearing defect window") assuring that the correlation between bearing defects and axle counts is accurate.

The circuitry of the aforementioned references is used to analyze the sounds generated by a loudspeaker on one side of the track as detected by the acoustic sensor mounted on the opposite side of the track. The gain of the circuitry can be analyzed and set to compensate for changes in response of the circuitry or atmospheric conditions, etc. The microprocessor monitors this circuitry for the generation of an alarm appropriate for the simulated characteristic acoustic signature. This inherently tests the electronic as well as the mechanical functioning of the apparatus, such as the opening of the shutters which protect the acoustic sensor.

Each monitored characteristic acoustic signature can be automatically generated so as to test the equipment fully. Typically, the simulated acoustic signatures of all relevant frequencies are sequentially generated in one loudspeaker across the track from one acoustic sensor (simulating bearing defects on a first side of the train), then the same or similar signatures are sequentially generated in the other loudspeaker (simulating bearing defects on a second side of the train). If a proper alarm is ever not generated, an appropriate message is transmitted as a warning to cognizant personnel, either at the location of the apparatus or at a centralized location, so that appropriate action can be taken.

Alternately, for trouble-shooting, individual defect frequencies can be effected in a manual entry mode to facilitate signal tracing and localization of problems in order for the technician to determine the appropriate corrective action. Moreover, these messages may be stored in the apparatus or sent automatically or as requested to a centralized location.

BRIEF DESCRIPTION OF THE DRAWINGS

Further objects and advantages of the invention will become apparent from the following description and claims wherein:

FIG. 3 shows the timing of the expected delay zone for the roller defect test.

DETAILED DESCRIPTION OF THE PREFERRED EMBODIMENT

Figure 1:
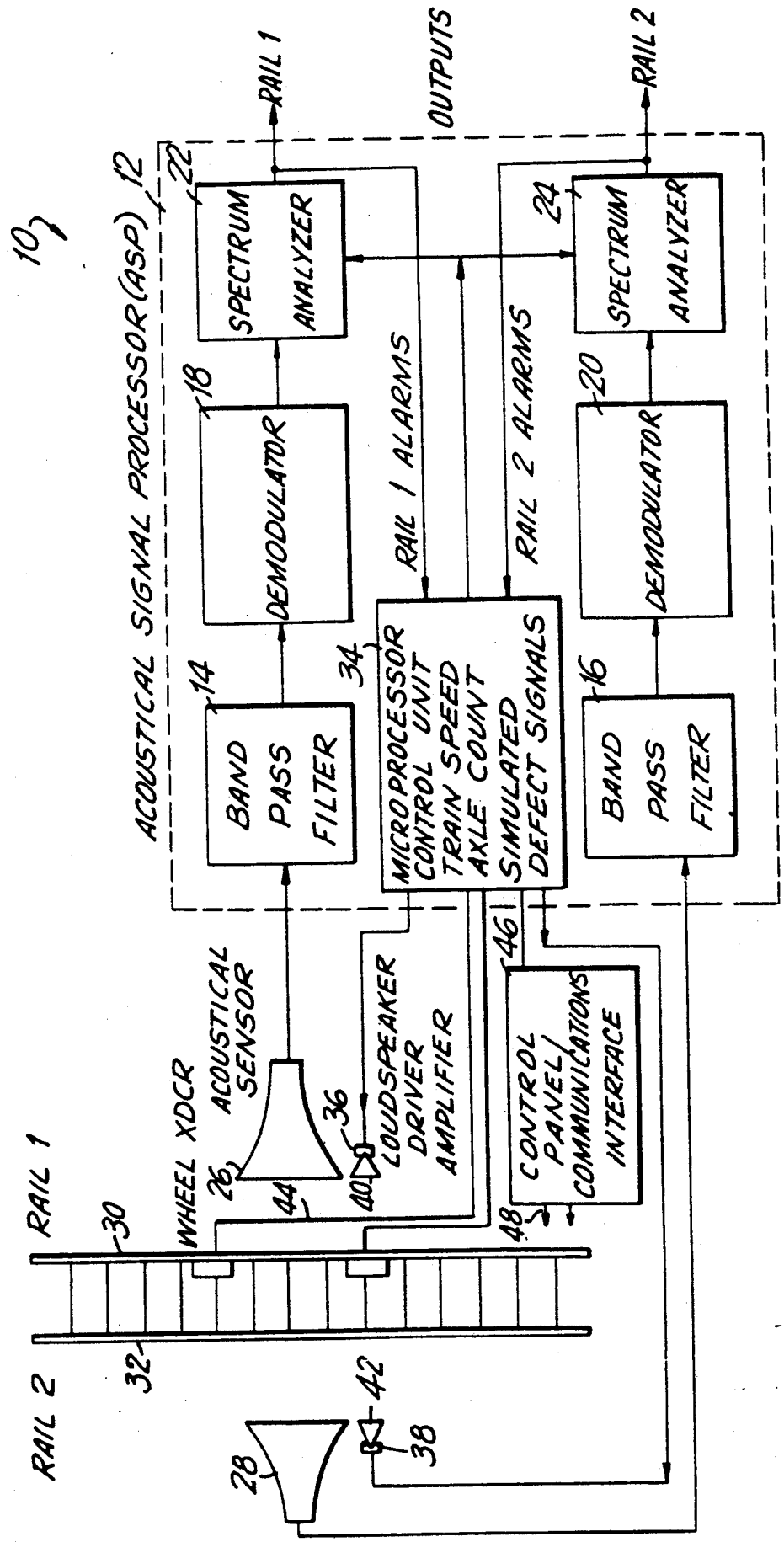
FIG. 1 shows a schematic of the present invention.

Referring now to the drawings, FIG. 1 is a schematic of the apparatus 10 of the present invention. Acoustic signal processor 12 includes bandpass filters 14, 16, demodulators 18, 20 and spectrum analyzers 22, 24 which are representative of the circuitry disclosed in the aforementioned references (U.S. Pat. Nos. 4,790,190 and 4,843,885 and pending patent application Ser. No. 367,890). Sensors 26, 28 (also representative of the circuitry disclosed in the aforementioned references) are placed so as to be responsive to railroad car bearings traversing rails 30, 32. Bandpass filters 14, 16 receive electrical signals from acoustic sensors 26, 28 and remove low and high frequency noise away from the carrier frequency. Demodulators 18 and 20 remove the carrier frequency thereby extracting an envelope from the output of bandpass filters 14 and 16. Spectrum analyzers 22, 24 extract and then compare the frequency spectrum of the envelope to the characteristic impact frequencies of the various bearing defect type/bearing size/wheel diameter/train speed combinations.

The testing of this apparatus is implemented by a microprocessor 34 which controls driver amplifier means 36, 38 of loudspeakers 40, 42. Microprocessor 34 communicates with spectrum analyzers 22, 24 by sending train speed signals to and receiving alarm signals from spectrum analyzers 22, 24. These train speed signals are simulated during testing but are responsive to signals from the train speed/axle count sensor 44 during normal operation.

Microprocessor 34 is responsive to control panel/communications interface 46 wherein remote or local commands can be entered for testing and the results of the testing appropriately transmitted. For remote testing, control panel/communications interface 46 may communicate with the user or a centralized computer via telephone lines 48.

Automatic self-testing is preferred either immediately before or immediately after the passage of a train so as to confirm the integrity of the monitoring results for the train. Alternately, microprocessor 34 may include timing means to effect regular implementation of the apparatus 10. All testing is automatically aborted during the presence of a train so that the equipment may operate to detect defects.

In order to use apparatus 10 for integrity testing without timed generation of the simulated acoustic signatures, the appropriate command is entered into control panel/communications interface 46 when a train is not present.

In the automatic self-testing mode, simulated characteristic acoustic signatures are first sequentially generated by loudspeaker 42 and sensed by acoustic sensor 26 so as to simulate defects on wheels or bearings traversing the first rail 30. Then simulated acoustic signatures are sequentially generated by loudspeaker 40 and sensed by acoustic sensor 28 so as to simulate defects on wheels or bearings traversing the second rail 32. Acoustic sensor 26 and loudspeaker 40 are enclosed in a first housing adjacent to first rail 30 while acoustic sensor 28 and loudspeaker 42 are enclosed in a second housing adjacent to second rail 32.

In order to generate these simulated characteristic acoustic signatures, microprocessor 34 chooses an appropriate simulated characteristic acoustic signature of a bearing defect at a given train speed including, if necessary, the appropriate modulating carrier frequency and transmits an electrical signal representative of the signature to driver amplifier means 36 or 38. This causes the simulated characteristic acoustic signal to be generated by loudspeakers 40 or 42 so as to be picked up by acoustic sensors 28 or 26, respectively. Driver amplifier means 36 and 38 are driven at separate times so as to provide interference free testing for each channel. Microprocessor 34 sends an appropriate train speed signal to spectrum analyzer 22 or 24 so as to program the filters therein for the simulated train speed. If the spectrum analyzer 22 or 24 properly detects the amplitude and frequency of the simulated characteristic signal, an alarm is generated and transmitted back to microprocessor 34. If the expected alarm is not generated, then microprocessor 34 signals control panel/communications interface 46 so that the technician, user or central computer (not shown) can be appropriately alerted. Furthermore, spectrum analyzer 22 or 24 may include means for monitoring and adjusting the gain of apparatus 10. If apparatus 10 is in the automatic test mode, a series of these processes, each corresponding to a different bearing defect type/bearing size/wheel diameter/train speed combination, is performed.

Figure 2:
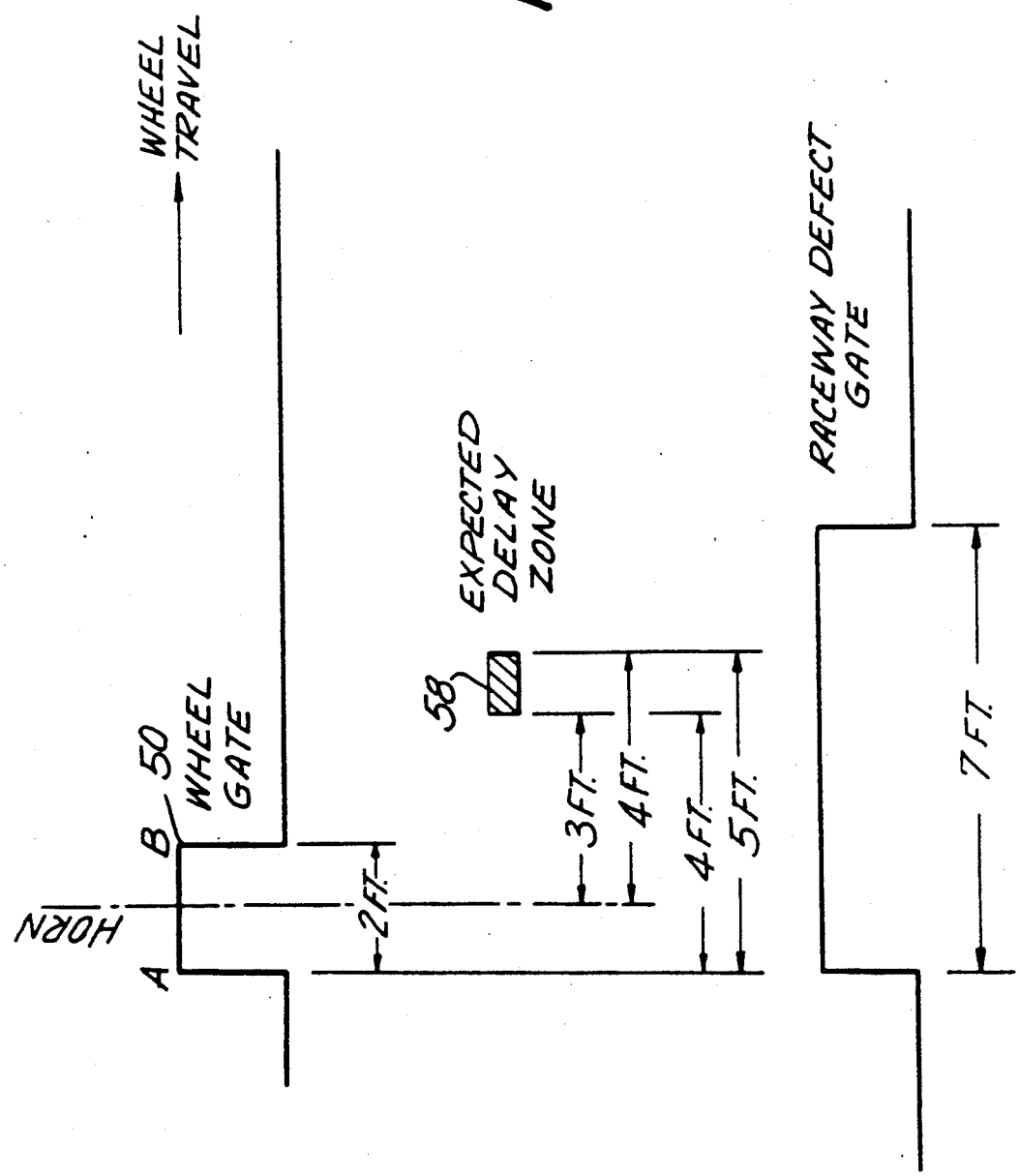
FIG. 2 shows the timing of the expected delay zone for the raceway defect test.

The use of apparatus 10 with timed generation of the simulated acoustic signatures is similar to the above description except that the characteristic acoustic signature generated by the loudspeakers is timed so as to occur during a wheel gate 50 (A·B) corresponding to two feet at the simulated train speed. That signal is expected to fall within the raceway defect gate 54 for an actual wheel (i.e., such as zone 58). More specifically, as shown in FIGS. 2 and 3, microprocessor 34 generates (either by calculation or retrieval from a table) a simulated wheel gate 50 corresponding to about two feet in width at the given train speed with raceway defect gate 54 corresponding to about 7 feet at the given train speed. Expected processing delay zone 58 is included within the gate 54. In order for the test to be satisfactory, not only must the detected signal be of the proper amplitude and frequency, but the resulting alarm which lies within the expected delay zone 58 must also fall within the raceway gate 54. This helps assure that during use of apparatus 10 to monitor the bearing of a railroad train that the correlation between bearing defects and axle counts is accurate thereby enabling a repair crew to locate the defective bearing quickly and accurately.

Obviously, numerous modifications may be made to the apparatus without departing from the scope of the invention as defined in the appended claims.

What is claimed is:

1. In an apparatus for monitoring bearings of a railway train for defects during operation of the train along a section of track said apparatus being of the type including train speed sensing means, means for transducing acoustic vibrations in said bearings into an electric signal, means for filtering the electric signal, and means for spectrum analyzing the electric signal, the improvement comprising means for automatically generating successive simulated characteristic acoustic signatures of various gearing defect types/bearing size/wheel diameter/train speed combinations and means for detecting expected alarm signals from said spectrum analyzing means in response to said simulated characteristic acoustic signatures.

2. The apparatus in accordance with claim 1 further comprising communicating means responsive to said means for detecting expected alarm signals.

3. The apparatus in accordance with claim 2 wherein said communicating means communicates a malfunction, as indicated by a lack of an expected alarm signal.

4. The apparatus in accordance with claim 3 wherein said communicating means communicates a location of the apparatus when communicating the malfunction.

5. The apparatus in accordance with claim 2 wherein said communication means communicates via telephone lines.

6. The apparatus in accordance with claim 1 further including means for aborting said generated characteristic acoustic signatures in the presence of a train along the section of track.

7. The apparatus in accordance with claim 1 wherein said spectrum analyzing means is responsive to means for producing a simulated train speed signal corresponding to said simulated characteristic acoustic signature.

8. The apparatus in accordance with claim 1 wherein said means for generating simulated characteristic acoustic signatures includes a microprocessor, amplification means responsive to said microprocessor and at least one loudspeaker responsive to said amplification means.

9. The apparatus in accordance with claim 8 including two loudspeakers and wherein said means for transducing includes two acoustic sensors, one of said acoustic sensors and one of said loudspeakers being placed on each side of the section of track and wherein said acoustic sensors are responsive to said loudspeakers on the respective opposite side of the section of track.

10. The apparatus in accordance with claim 9 wherein one of said loudspeakers and one of said acoustic sensors are in a first housing and the other of said loudspeakers and sensors are in a second housing.

11. The apparatus in accordance with claim 9 wherein said means for generating automatically generates successive simulated characteristic acoustic signatures in a first of said two loudspeakers while a second of said two loudspeakers is silent, and then generates successive simulated characteristic acoustic signatures in the second of said two loudspeakers while the first of said two loudspeakers is silent.

12. The apparatus in accordance with claim 11 further including means for comparing a level of the electric signal with an expected value.

13. The apparatus in accordance with claim 12 further including means for adjusting gain applied to the electric signal responsive to said means for comparing.

14. The apparatus in accordance with claim 1 wherein said simulated characteristic acoustic signatures are generated for a pre-selected period corresponding to a wheel gate and said means for detecting expected alarms includes timing means to determine if the expected alarms are within an expected delay zone.

15. The apparatus in accordance with claim 1 further including a timing means for periodically initiating operation of said means for generating simulated characteristic acoustic signatures.

16. The apparatus in accordance with claim 8 wherein said microprocessor includes a timing means for periodically initiating operation of said means for generating simulated characteristic acoustic signatures.

17. The apparatus in accordance with claim 1 further including means for initiating operation of said means for generating simulated characteristic acoustic signatures immediately prior to and immediately after passage of the railway train on the section of track.

* * * * *